(12) United States Patent
Noble et al.

(10) Patent No.: US 6,719,961 B1
(45) Date of Patent: Apr. 13, 2004

(54) USE OF CHITOSAN TO DECREASE SKIN IRRITATION CAUSED BY SHAVING

(75) Inventors: Bill W. Noble, Greenville, SC (US); Virginia Lazarowitz, Hatfield, PA (US); Timothy C. Morris, Morton, PA (US)

(73) Assignee: Cognis Corporation, Cincinnati, OH (US)

( * ) Notice: Subject to any disclaimer, the term of this patent is extended or adjusted under 35 U.S.C. 154(b) by 60 days.

(21) Appl. No.: 09/713,974

(22) Filed: Nov. 16, 2000

Related U.S. Application Data

(60) Provisional application No. 60/169,509, filed on Dec. 7, 1999.

(51) Int. Cl.$^7$ ............................. A61K 7/15; A61K 7/00; C08B 37/08; B26B 19/00
(52) U.S. Cl. ........................ 424/47; 424/73; 424/489; 536/20; 30/41
(58) Field of Search ............................. 424/73, 489, 47; 30/41; 536/20

(56) References Cited

U.S. PATENT DOCUMENTS

| | | | | |
|---|---|---|---|---|
| 2,818,872 A | * | 1/1958 | Wang | 132/289 |
| 4,966,754 A | * | 10/1990 | Purohit et al. | 424/195.1 |
| 5,643,672 A | * | 7/1997 | Marchi et al. | 428/402 |
| 5,690,924 A | * | 11/1997 | Keil et al. | 429/78.03 |
| 5,903,979 A | | 5/1999 | Oldroyd | 30/41 |
| 6,093,386 A | * | 7/2000 | Sampino et al. | 424/73 |
| 6,130,321 A | * | 10/2000 | Johnson et al. | 536/20 |
| 6,183,766 B1 | * | 2/2001 | Sine et al. | 424/405 |

* cited by examiner

*Primary Examiner*—Sreeni Padmanabhan
*Assistant Examiner*—Gina C Yu
(74) *Attorney, Agent, or Firm*—John E. Drach; Steven J. Trzaska

(57) ABSTRACT

A process for decreasing skin irritation caused by shaving involving contacting the skin with a composition containing chitosan.

18 Claims, No Drawings

USE OF CHITOSAN TO DECREASE SKIN IRRITATION CAUSED BY SHAVING

CROSS-REFERENCE TO RELATED APPLICATIONS

This application claims the benefit of copending provisional application Ser. No. 60/169,509 filed on Dec. 7, 1999.

STATEMENT REGARDING FEDERALLY SPONSORED RESEARCH OR DEVELOPMENT

NOT APPLICABLE.

BACKGROUND OF THE INVENTION

The present invention generally relates to a process for decreasing skin irritation caused by the removal of hair from human skin. As a preliminary step to shaving, it is common practice to apply a shaving preparation to the skin, such as a shaving soap or the like in order to facilitate the shaving operation. This is done in order to lubricate the skin, thus enabling the razor to slide more easily over the skin, thereby decreasing its degree of irritation.

In some situations, however, the skin may not be adequately protected against irritation. Moreover, during the shaving operation most of the preparation is removed, thereby further enhancing the likelihood of skin irritation. Thus, it has been found to be advantageous to lubricate the skin immediately following the shaving operation.

One way of doing so is to apply an after-shave preparation in order to lubricate the skin. Another way involves providing the razor with a means for delivering a shaving enhancement composition or medium during the shaving process. Thus, it is known to provide a blade unit with a strip of material from which a lubricant is very gradually leached out during the shaving process. The benefits of both an after-shave preparation and lubricating strip on the razor have been well proven, but the active materials which can be incorporated in them is limited by the manufacturing process, and the rate at which the lubricant may be discharged, i.e., the rate may be so low that an effective preparation of the skin before shaving may still be needed.

BRIEF SUMMARY OF THE INVENTION

The present invention is directed to a process for decreasing skin irritation caused shaving involving contacting skin with a chitosan compound having a molecular weight ranging from about 1,000 to about 25,000,000, and a particle size of from about 0.01 to about 50 microns.

BRIEF DESCRIPTION OF THE SEVERAL VIEWS OF THE DRAWING

NOT APPLICABLE.

DETAILED DESCRIPTION OF THE INVENTION

Other than in the operating examples, or where otherwise indicated, all numbers expressing quantities of ingredients or reaction conditions are to be understood as being modified in all instances by the term "about".

Chitosan is derived from chitin by deacetylation. Chitin itself is typically obtained from conventional sources such as crustacean outer shells and fungal mycelial mats. Chitin and chitosan refer to a family of compounds that exhibit widely differing physical and chemical properties. These differences are due primarily to the products' varying molecular weights, degrees of acetylation and presence of contaminants such as covalently bound, species-specific proteins, single amino acid and inorganic contaminants.

Though any type of chitosans, in general, may be used by the present invention, particularly preferred chitosans are those having molecular weights ranging from about 1,000 to about 25,000,000, and preferably from about 500,000 to about 5,000,000 g/mol, and a particle size of from about 0.1 to about 50 microns, preferably from about 0.1 to about 40, and most preferably from about 0.1 to about 10 microns.

The chitosan compound of the present invention may be employed either in the form of a solid or a liquid. Its application in solid form onto an area of the skin requiring shaving may be accomplished in a number of ways.

Thus, according to one embodiment of the present invention, the chitosan component can take the form of a solid powdery strip, preferably present on a razor device. The chitosan strip may be located above the blade portion on the razor in order to for it to be applied immediately subsequent to the shaving operation. Based on this positioning, as the blade portion of the razor shaves hair from the skin, the chitosan strip would then contact the skin immediately thereafter, resulting in the chitosan being applied thereon. This method of application involves the use of so-called "safety razors".

Conversely, the chitosan strip may be located below the razor in the event that one would wish to apply the chitosan onto the skin immediately prior to shaving. Based on this positioning, the chitosan strip would contact the skin immediately before the blade portion shave hair from the skin, resulting in a shaving pre-treatment step.

It should be noted, however, that the solid powdery chitosan need not be located on the razor body itself in order for it to be used. Any suitable dispensing device may be employed without departing from the spirit of the invention, namely, to treat skin either prior to, or after, a shaving operation.

The solid powdery chitosan composition of the present invention will typically comprise components other than the chitosan itself. This is mainly due to cost considerations since chitosan itself is very expensive. A solid particulate component can be mixed with the chitosan to act as a filler for the solid powdery chitosan composition. There are a number of suitable solid particulate components which may be employed in the present invention including, but not limited to, talc, micas, modified or unmodified starch, silica, alumina, boron nitride, kaolin, zinc and titanium oxides, stearates, precipitated calcium carbonates, magnesium carbonate or hydrocarbonate, metallic soaps derived from a carboxylic organic acid having from 8 to 22 carbon atoms, synthetic polymer or (copolymer) powders such as polyethylenes, polyacrylates, polymethacrylates, polyesters, polyamides, and the like, and powders in the form of hollow microspheres made from thermoplastic materials whose hollow part may contain a gas.

In the event that a solid particulate component is employed in admixture with the chitosan component, it will typically be present in an amount of from about 0.1 to about 99% by weight, based on the weight of the composition.

Another auxiliary component which may be included is a binder/emollient which acts to both further enhance compaction/binding of the solid particulate component and provide added emolliency properties onto skin treated therewith.

Suitable binder/emollients which may be employed by the present invention include, but are not limited to, fatty acids, fatty alcohols, esters of fatty acids and fatty alcohols, Guerbet alcohols, waxes, silicones, alkanes, vegetable oils, mineral oils, animal oils such as lanolin, insect oils, humectants, glycols, starches, sugars, excipients, plasticizers, aromatic hydrocarbons, deionized water, aliphatic hydrocarbons, cyclic hydrocarbons, and the like.

In the event that a binder/emollient is employed, it can be present in the composition in an amount of from about 0.1 to about 99% by weight, preferably from about 1 to about 50% by weight, and most preferably from about 1 to about 25% by weight, based on the weight of the composition.

Various standard additives may also be incorporated into the invention including, but not limited to, preservatives; antiseptics such as trichlorodiphenyl ethers, boric acid, and the like) which are used especially in deodorant powders for the body and feet and in baby powders; astringent agents which are used in deodorant powders and in foot powders such as aluminum hydroxychloride and alum; anti-free radical agents; vitamins; demulcent agents; perfumes; consistency agents; anti-pruritics (anti-itch) and the like.

In the event that an additive is employed in the composition of the present invention, it will typically be present in an amount of from about 0.1 to about 99% by weight, based on the weight of the composition.

Finally, it may be desirable to employ the chitosan composition in the form of a liquid. In the event that a liquid chitosan composition is employed, any suitable solvent may be used as the carrier liquid for the chitosan. Examples thereof include, but are not limited to, water, propylene glycol, and glycerin, with the proviso that the pH is made acidic using, for example, a glycolic acid such as citric acid. The chitosan will be present in the liquid in the form of a dispersion. In the event that a liquid carrier component is employed, it will typically be present in the composition in an amount of from about 50 to about 99% by weight, preferably from about 70 to about 99% by weight, and most preferably from about 80 to about 99% by weight, based on the weight of the composition. The liquid chitosan composition may be applied onto the skin using any suitable dispensing means such as, for example, a reservoir capable of both storing and dispensing the liquid composition on demand. The reservoir itself may be constructed such that it is located on the razor unit itself, either above or below the blade.

It will be recognized by those skilled in the art that changes may be made to the above-described embodiments of the invention without departing from the broad inventive concepts thereof. It is understood, therefore, that the invention is not limited to the particular embodiments disclosed herein, but is intended to cover all modifications which are within the scope and spirit of the invention as defined by the appended claims.

What is claimed is:

1. A process for decreasing skin irritation caused by shaving comprising contacting the skin with a composition containing chitosan.

2. The process of claim 1 wherein the chitosan has a molecular weight of from about 1,000 to about 25,000,000 g/mol, and a particle size of from about 0.01 to about 50 microns.

3. The process of claim 1 wherein the composition is a solid powder.

4. The process of claim 1 wherein the composition further includes a solid particulate filler component.

5. The process of claim 4 wherein the solid particulate filler component is present in the composition in an amount of from about 0.1 to about 99% by weight.

6. The process of claim 1 wherein the composition further includes a binder component.

7. The process of claim 6 wherein the binder component is present in the composition in an amount of from about 0.1 to about 99% by weight, based on the weight of the composition.

8. The process of claim 1 wherein the composition further includes a liquid carrier component.

9. The process of claim 8 wherein the liquid carrier component is present in the composition in an amount of from about 50 to about 99% by weight, based on the weight of the composition.

10. The process of claim 6 wherein the composition is in the form of a solid powder strip located on a razor unit.

11. The process of claim 8 wherein the composition is in the form of a liquid present in a reservoir.

12. The process of claim 11 wherein the reservoir is located on a razor unit.

13. The process of claim 11 wherein the skin is contacted with the composition prior to shaving.

14. The process of claim 11 wherein the skin is contacted with the composition after shaving.

15. The process of claim 1 wherein the chitosan has a molecular weight of from about 500,000 to about 5,000,000 g/mol.

16. The process of claim 1 wherein the chitosan has a particle size of from about 0.1 to about 10 microns.

17. A safety razor blade unit having an area containing chitosan.

18. The safety razor blade of claim 17 wherein the chitosan is located either above or below a blade portion of the safety razor blade.

\* \* \* \* \*